United States Patent [19]

Guglielmetti

[11] 4,011,261

[45] Mar. 8, 1977

[54] PROCESS FOR THE MANUFACTURE OF 1,4-DISUBSTITUTED BICYCLIC OR TRICYCLIC COMPOUNDS AND NEW 1,4-DISUBSTITUTED BICYCLIC COMPOUNDS

[75] Inventor: Leonardo Guglielmetti, Basel, Switzerland

[73] Assignee: Ciba-Geigy Corporation, Ardsley, N.Y.

[22] Filed: Nov. 5, 1975

[21] Appl. No.: 629,180

[30] Foreign Application Priority Data

Nov. 14, 1974 Switzerland .................... 15190/74

[52] U.S. Cl. .................... 260/515 P; 260/293.85; 260/326.46; 260/326.62; 260/340.5; 260/465 D; 260/465 E; 260/465 F; 260/465 G; 260/465 H; 260/470; 260/473 F; 260/475 R; 260/475 FR; 260/507 R; 260/515 A; 260/515 M; 260/518 R; 260/520 D; 260/558 R; 260/558 S; 260/559 R

[51] Int. Cl.² .................... C07C 51/08; C07C 63/38

[58] Field of Search ....... 260/465 A, 515 P, 515 A, 260/515 M, 507 R, 518 R, 520, 340.5, 293.85, 326.46, 465 H

[56] References Cited

UNITED STATES PATENTS 3,277,154 10/1966 Vanderwerff .................... 260/515
3,287,403 11/1966 McNelis et al. ............... 260/515 X

*Primary Examiner*—Lewis Gotts
*Assistant Examiner*—Dolph H. Torrence
*Attorney, Agent, or Firm*—Joseph G. Kolodny; Edward McC. Roberts; Prabodh I. Almaula

[57] ABSTRACT

The present invention provides a new process for the manufacture of 1,4-disubstituted bicyclic or tricyclic compounds by reacting a 1,2-bis-cyanomethyl-benzene or 2,3-bis-cyanomethyl-naphthalene with glyoxal in the presence of a base and a solvent as well as new 1,4-disubstituted bicyclic compounds.

7 Claims, No Drawings

PROCESS FOR THE MANUFACTURE OF 1,4-DISUBSTITUTED BICYCLIC OR TRICYCLIC COMPOUNDS AND NEW 1,4-DISUBSTITUTED BICYCLIC COMPOUNDS

The present invention provides a process for the manufacture of 1,4-disubstituted bicyclic or tricyclic compounds and also provides new 1,4-disubstituted bicyclic or tricyclic compounds.

Processes for the manufacture of 1,4-dicyanonaphthalenes which are unsubstituted in 2- and 3-position have already been disclosed in the literature. The disadvantage of these processes is that the end products can only be obtained by means of an alkali cyanide or alkali ferrocyanide melt which is effected at high temperatures with great difficulty, or from 1,4-dihalonaphthalenes which are not readily accessible. Such processes are described, for example, in A. 152, 309; B. 55, 120; J. Chem. Soc. 1936, 1739–44, or Monatsch. Chem. 83, 865–69, 1952.

U.S. Pat. No. 3,652,667 describes the manufacture of naphthalene-1,4-dicarboxylic acid by oxidation of 1-methyl-4-acetylnaphthalene with excess alkali dichromate at elevated temperature and under pressure. In this process, 1-methyl-4-acetyl-naphthalene must be manufactured from 1-methyl-naphthalene and acetyl chloride by a Friedel-Crafts reaction. The disadvantages of this process are that the oxidation is difficult to perform, the starting materials are hard to obtain, and the use of substantial excesses of alkali dichromates creates ecological problems.

The present invention is based on the surprising observation that it is possible to obtain 1,4-disubstituted bicyclic or tricyclic compounds while avoiding these disadvantages.

The present invention provides in the first instance a process for the manufacture of 1,4-dicyano-substituted bicyclic or tricyclic compounds of formula

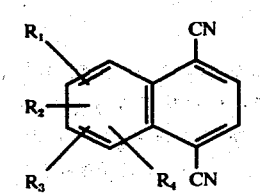

(I)

wherein $R_1$ represents hydrogen, halogen, alkyl, alkoxy, carboxy, carbalkoxy, -$CONR_5R_6$, wherein each of $R_5$ and $R_6$ independently represents hydrogen or alkyl, or together they complete a 5- or 6-membered heterocyclic ring, sulpho, —$SO_2NR_5R_6$, wherein $R_5$ and $R_6$ are as defined hereinbefore, alkylsulphonyl, arylsulphonyl, cyano, nitro, or together with $R_2$ completes a 6-membered aromatic ring or represents the methylenedioxy radical, $R_2$ represents hydrogen, halogen, alkyl, alkoxy, carboxy, carbalkoxy, —$CONR_5R_6$, wherein $R_5$ and $R_6$ are as defined hereinbefore, alkylsulphonyl, nitro, or together with $R_1$ completes a 6-membered aromatic ring or represents the methylenedioxy radical, $R_3$ represents hydrogen, halogen, or alkyl, and $R_4$ represents hydrogen, halogen or alkyl, which process comprises reacting an o-xylylene dicyanide of formula

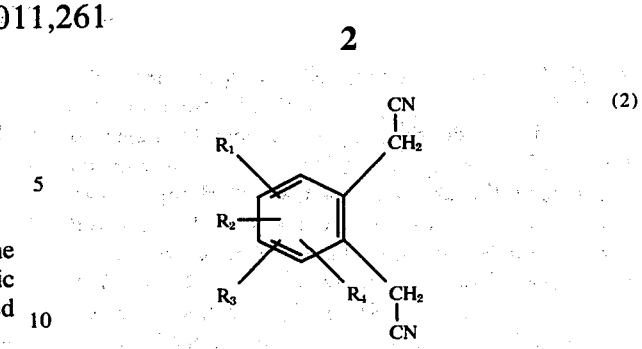

wherein $R_1$, $R_2$, $R_3$ and $R_4$ are as defined hereinbefore, with glyoxal in the presence of a base and a solvent at temperatures below 50° C.

The reaction is carried out, for example, at temperatures between −20° and +40° C, preferably between 0° and 30° C.

Suitable halogens are fluorine, chlorine and bromine, preferably chlorine. Alkyl, alkoxy and carbalkoxy radicals $R_1$, $R_2$, $R_3$ and $R_4$ contain 1 to 18, preferably 1 to 6, carbon atoms. The alkyl radicals $R_5$ and $R_6$ and alkylsulphonyl radicals contain preferably 1 to 4 carbon atoms. A suitable arylsulphonyl radical is in particular the phenylsulphonyl radical.

Carboxy is to be understood as meaning the radical —COOM and sulpho the radical —$SO_3M$, wherein M represents hydrogen or a salt-forming cation, such as that of sodium, potassium, calcium, barium or magnesium, and also that of ammonium which is unsubstituted or substituted by alkyl or hydroxyalkyl of 1 to 4 carbon atoms. Besides hydrogen, M preferably represents the potassium and sodium cation.

Suitable bases are inorganic and organic compounds, for example those of lithium, sodium, potassium, rubidium, cesium or ammonium, for example hydroxides and alcoholates thereof, or tertiary amines, such as lithium, sodium or potassium hydroxide, sodium or potassium methylate, sodium or potassium ethylate, triethylamine or pyridine.

Suitable solvents are aprotic and protic solvents, preferably water-miscible organic solvents, for example methanol, ethanol, isopropanol, butanols, dioxan and dimethyl formamide.

The reaction is advantageously carried out in an anhydrous organic solvent, preferably one in which the base is partially or completely soluble.

The glyoxal used as starting material can be used either in the form of its ordinary commercially available aqueous solution, e.g. 30% or 40% aqueous solution, or in the form of a compound that liberates glyoxal under the reaction conditions, for example trimeric and polymeric glyoxal, glyoxal bisulphite, glyoxal sulphate and glyoxal acetals.

Within the scope of this first feature of the invention, an interesting process is that for the manufacture of 1,4-dicyano-substituted bicyclic or tricyclic compounds of formula

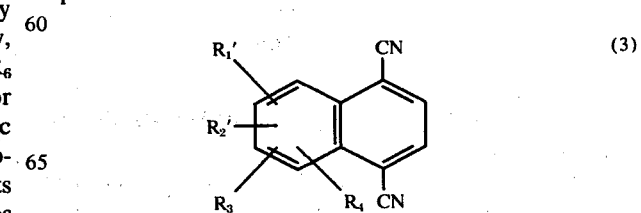

(3)

wherein $R_1'$ represents hydrogen, halogen, alkyl, alkoxy, carboxy, carbalkoxy, —$CONR_5R_6$, wherein each of $R_5$ and $R_6$ independently represents hydrogen or alkyl or together they complete a 5- or 6-membered heterocyclic ring, alkylsulphonyl, arylsulphonyl, cyano, nitro, or together with $R_2'$ completes a 6-membered aromatic ring or represents the methylenedioxy radical, $R_2'$ represents hydrogen, halogen, alkyl, alkoxy, alkylsulphonyl, or together with $R_1'$ completes a 6-membered aromatic ring or represents the methylene dioxy radical, and $R_3$ and $R_4$ are as defined hereinbefore, which comprises reacting an o-xylylene dicyanide of formula

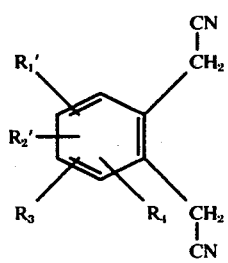

(4)

wherein $R_1'$, $R_2'$, $R_3$ and $R_4$ are as defined hereinbefore, with glyoxal.

A preferred process is that for the manufacture of 1,4-dicyano-substituted bicyclic or tricyclic compounds of formula

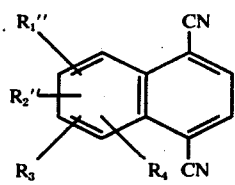

(5)

wherein $R_1''$ represents hydrogen, halogen, alkyl, alkylsulphonyl, arylsulphonyl, or together with $R_2''$ completes a 6-membered aromatic ring, $R_2''$ represents hydrogen, halogen, alkyl, alkylsulphonyl, or together with $R_1''$ completes a 6-membered aromatic ring, $R_3$ represents hydrogen, halogen, or alkyl, and $R_4$ represents hydrogen, halogen or alkyl, which comprises reacting an o-xylylene dicyanide of formula

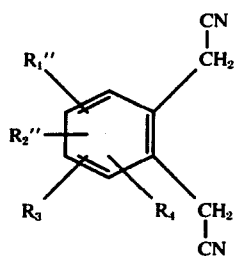

(6)

wherein $R_1''$, $R_2''$, $R_3$ and $R_4$ are as defined hereinbefore, with glyoxal.

A preferred process is also that for the manufacture of 1,4-dicyano-substituted bicyclic or tricyclic compounds of formula

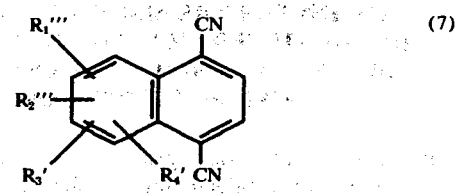

(7)

wherein $R_1'''$ represents hydrogen, halogen, alkyl, or together with $R_2'''$ completes a 6-membered aromatic ring, $R_2'''$ represents hydrogen, halogen, alkyl, or together with $R_1'''$ completes a 6-membered aromatic ring, $R_3'$ represents hydrogen or halogen, $R_4'$ represents hydrogen or halogen, which comprises reacting an o-xylylene dicyanide of formula

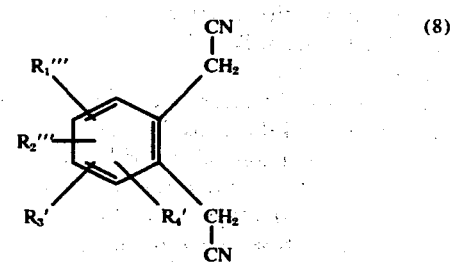

(8)

wherein $R_1'''$, $R_2'''$, $R_3'$ and $R_4'$ are as defined hereinbefore, with glyoxal, and for the manufacture of 1,4-dicyano-substituted naphthalenes of formula

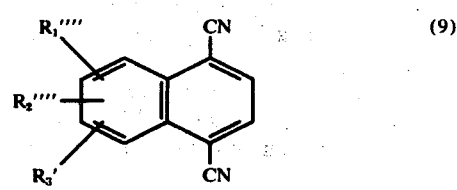

(9)

wherein $R_1''''$ represents hydrogen, halogen or alkyl, $R_2''''$ represents hydrogen, halogen or alkyl, and $R_3'$ represents hydrogen or halogen, which comprises reacting an o-xylylene dicyanide of formula

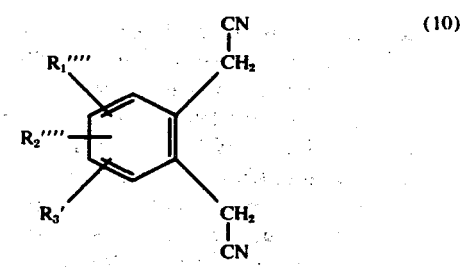

(10)

wherein $R_1''''$, $R_2''''$ and $R_3'$ are as defined hereinbefore, with glyoxal.

A particularly preferred process is that the manufacture of 1,4-dicyano-substituted naphthalenes of formula

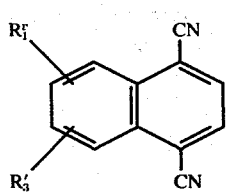

wherein $R_1^v$ represents hydrogen or halogen and $R_3'$ represents hydrogen or halogen, which comprises reacting an o-xylylene dicyanide of formula

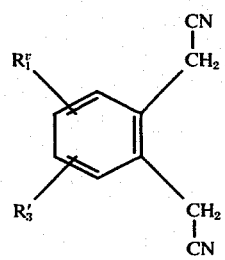

wherein $R_1^v$ and $R_3'$ are as defined hereinbefore, with glyoxal.

Within the scope of formulae (1) to (12), preferred compounds are those wherein one of the four symbols $R_1$, $R_2$, $R_3$ or $R_4$, or one of the symbols derived therefrom, represents hydrogen. Of particular importance are compounds wherein three of these symbols represent hydrogen.

The most preferred process is that for the manufacture of 1,4-dicyanonaphthalene of formula

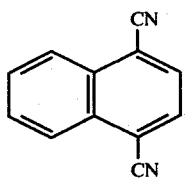

wherein o-xylylene dicyanide of formula

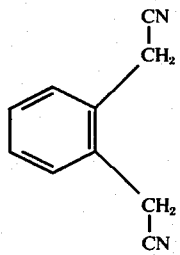

is reacted with glyoxal.

The o-xylylene dicyanides used as starting materials can be obtained very easily and in very good yields from the corresponding o-xylylene dihalides by reaction with alkali cyanides. For example, o-xylylene dicyanide is obtained direct by reacting o-xylylene dibromide with potassium cyanide in 70% yield of pure recrystallised product (J.O. Halford and B. Weissmann, J. Org. Chem. 17, 1649, (1952); E. J. F. Atkinson and J. F. Thorpe, J. Chem. Soc. 91, 1699, (1907)). The o-xylylene dihalides can in turn be obtained by known processes either by direct halogenation of o-xylene or by halomethylation of toluene or benzyl chloride and separation of o- and p-xylylene dichlorides by distillation (I.G. Farbenindustrie AG, PB 580 No. 5:PB 14998 No's. 94, 99 and 100).

By means of the above described process it has become possible to obtain in simple manner and in good yield a number of partly known compounds which so far have only been accessible by methods not easy to carry out. It is also possible to obtain new compounds by the novel process, for example those encompassed by the formulae (1), (3), (5), (7), (9) and (11).

The compounds of formulae (1), (3), (5), (7), (9), (11) and (13) which can be obtained according to the present invention can be used as intermediates for the manufacture of fluorescent brighteners, fluorescent dyes, dyes and plastics, after they have been saponified, if desired, to give the corresponding 1,4-naphthalenedicarboxylic acid derivatives. Examples of such fluorescent brighteners are cited in German Offenlegungsschrift No. 2,237,874 and in U.S. Pat. No. 3,709,896, and the use of naphthalene-1,4-dicarboxylic acid for the manufacture of polyamides is described in French patent No. 876,655.

The conversion of the 1,4-dicyano-substituted compounds of formulae (1), (3), (5), (7), (9), (11) and (13) in the corresponding 1,4-dicarboxylic acids is effected in known manner by alkaline or acid saponification.

In its second feature, the present invention provides a process for the manufacture of bicyclic or tricyclic compounds of formula

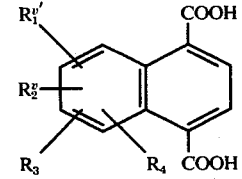

wherein $R_1^{v'}$ represents hydrogen, halogen, alkyl, alkoxy, carboxy, sulpho, $-SO_2NR_5R_6$, wherein each of $R_5$ and $R_6$ independently represents hydrogen or alkyl or together they complete a 5- or 6-membered heterocyclic ring, alkylsulphonyl, arylsulphonyl, nitro, or together with $R_2^v$ completes a 6-membered aromatic ring or represents the methylenedioxy radical, $R_2^v$ represents hydrogen, halogen, alkyl, alkoxy, carboxy, alkylsulphonyl, nitro, or together with $R_1^{v'}$ completes a 6-membered aromatic ring or represents the methylenedioxy radical, $R_3$ represents hydrogen, halogen or alkyl, and $R_4$ represents hydrogen, halogen or alkyl, which comprises reacting an o-xylylene dicyanide of formula

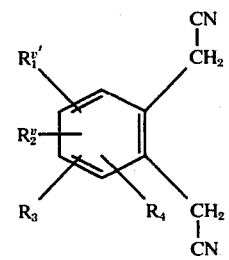

wherein $R_1^{v'}$, $R_2^v$, $R_3$ and $R_4$ are as defined hereinbefore, with glyoxal in the presence of a base and a solvent, and saponifying the resultant reaction product, without isolating it, at temperatures above 50° C with an acid or a base.

Suitable bases are inorganic and organic compounds, for example those of lithium, sodium, potassium, rubidium, cesium or ammonium, for example the hydroxides, alcoholates or tert. amines, such an lithium, sodium or potassium hydroxides, sodium or potassium methylate, sodium or potassium ethylate, triethylamine or pyridine.

Suitable solvents are water and organic, preferably water-miscible higher boiling solvents, for example those that boil between 50° and 210° C, such as mono- or polyhydric alcohols, for example propyl alcohols, butyl alcohols, ethylene glycol, 1,2-propane diol and glycerol.

Suitable mineral acids for the acid saponification are, for example, hydrochloric acid, sulphuric acid and phosphoric acid as well as aliphatic carboxylic acids, for example acetic and propionic acid. The saponification is carried out in the presence of water, preferably at reflux temperature.

Glacial acetic acid can be used as solvent or diluent for cyanides which are sparingly soluble.

The 1,4-dicarboxylic acid derivatives are obtained in this process in great purity and almost colourless. The free dicarboxylic acids can be reacted by methods which are known per se to yield corresponding derivatives, for example salts, esters, amides or halides.

Within the scope of this second feature of the invention, an interesting process is that for the manufacture of bicyclic or tricyclic compounds of formula

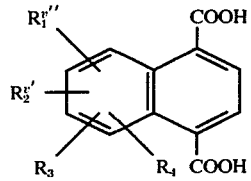

(17)

wherein $R_1^{v''}$ represents hydrogen, halogen, alkyl, carboxy, alkylsulphonyl, arylsulphonyl, nitro, or together with $R_2^{v'}$ completes a 6-membered aromatic ring or represents the methylenedioxy radical, $R_2^{v'}$ represents hydrogen, halogen, alkyl, alkoxy, alkylsuphonyl, or together with $R_1^{v''}$ completes a 6-membered aromatic ring or represents the methylenedioxy radical, $R_3$ represents hydrogen, halogen or alkyl, and $R_4$ represents hydrogen, halogen or alkyl, and of compounds of formula

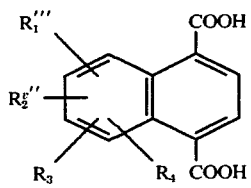

(18)

wherein $R_1^{v'''}$ represents hydrogen, halogen, alkyl, alkylsulphonyl, arylsulphonyl, or together with $R_2^{v''}$ completes a 6-membered aromatic ring, $R_2^{v''}$ represents hydrogen, halogen, alkyl, alkylsulphonyl, or together with $R_1^{v'''}$ completes a 6-membered aromatic ring, $R_3$ represents hydrogen, halogen, or alkyl, and $R_4$ represents hydrogen, halogen or alkyl, which process comprises reacting an o-xylylene dicyanide of formula

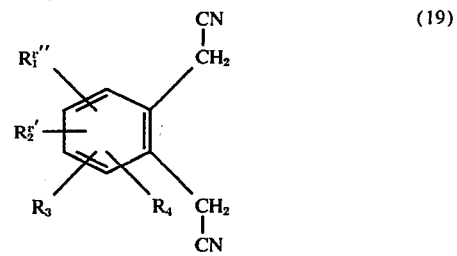

(19)

wherein $R_1^{v'''}$, $R_2^{v'}$, $R_3$ and $R_4$ are as defined hereinbefore, and of formula

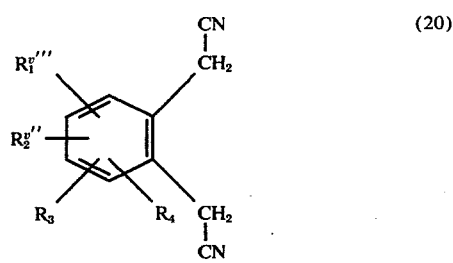

(20)

wherein $R_1^{v''''}$, $R_2^{v'''}$, $R_3$ and $R_4$ are as defined hereinbefore, with glyoxal.

Within the scope of this second feature of the invention, a preferred process is that for the manufacture of compounds of formula

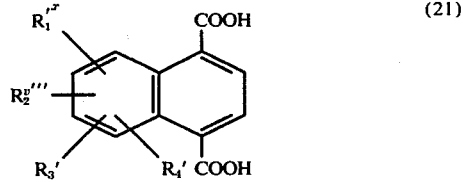

(21)

wherein $R_1'^x$ represents hydrogen, halogen or alkyl, or together with $R_2^{v''''}$ completes a 6-membered aromatic ring, $R_2^{v''''}$ represents hydrogen, halogen, alkyl or together with $R_1'^x$ completes a 6-membered aromatic ring, $R_3'$ represents hydrogen or halogen, and $R_4'$ represents hydrogen or halogen, and, in particular, of naphthalene-1,4-dicarboxylic acids of formula

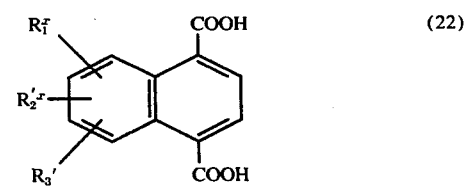

(22)

wherein $R_1^x$ represents hydrogen, halogen or alkyl, $R_2'^x$ represents hydrogen, halogen or alkyl, and $R_3'$ represents hydrogen or halogen, as well as those of formula

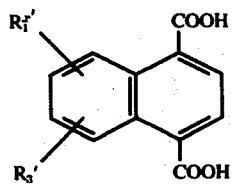
(23)

wherein $R_1^{x'}$ represents hydrogen or halogen and $R_3'$ represents hydrogen or halogen, which comprises reacting an o-xylylenedicyanide of formula

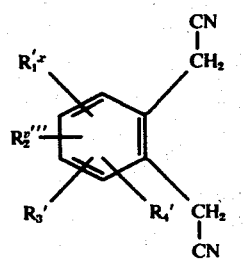
(24)

wherein $R_1'^x$, $R_2^{v'''}$, $R_3'$ and $R_4'$ are as defined hereinbefore, of formula

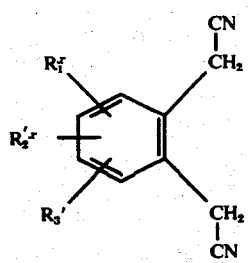
(25)

wherein $R_1^x$, $R_2'^x$ and $R_3'$ are as defined hereinbefore, or of formula

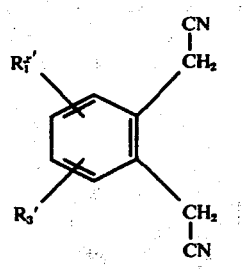
(26)

wherein $R_1^{x'}$ and $R_3'$ are as defined hereinbefore, with glyoxal.

Within the scope of the second feature of the present invention, a particularly preferred process is that for the manufacture of the naphthalene-1,4-dicarboxylic acid of formula

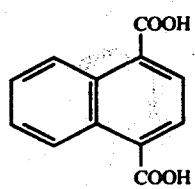
(27)

wherein an o-xylylene dicyanide of formula

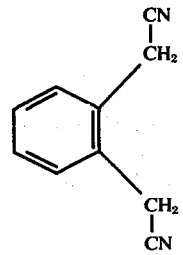
(28)

is reacted with glyoxal.

Also of interest within the scope of the present invention are 1,4-dicyano-substituted naphthalenes of formula

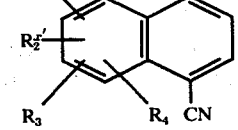
(29)

wherein $R_7$ represents halogen, alkyl, alkoxy, carboxy, carbalkoxy, —$CONR_5R_6$, wherein each of $R_5$ and $R_6$ independently represents hydrogen or alkyl, or together they complete a 5- or 6-membered heterocyclic ring, sulpho, —$SO_2NR_5R_6$, in which $R_5$ and $R_6$ are as defined hereinbefore, alkylsulphonyl, arylsulphonyl, cyano or nitro, $R_2^x$ represents hydrogen, halogen, alkyl, alkoxy, carboxy, carbalkoxy, —$CONR_5R_6$, wherein $R_5$ and $R_6$ are as defined hereinbefore, alkylsulphonyl or nitro, $R_3$ represents hydrogen, halogen or alkyl, and $R_4$ represents hydrogen, halogen or alkyl, and also 1,4-dicyano-substituted naphthalenes of formula

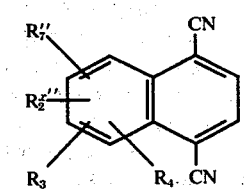
(30)

wherein $R_7'$ represents halogen, alkyl, alkoxy, carboxy, carbalkoxy, —$CONR_5R_6$ in which each of $R_5$ and $R_6$ independently represents hydrogen or alkyl or together they complete a 5- or 6-membered heterocyclic ring, alkylsulphonyl, arylsulphonyl, cyano or nitro, $R_2^{x'}$ represents hydrogen, halogen, alkyl, alkoxy or alkylsulphonyl, and $R_3$ and $R_4$ are as defined hereinbefore.

Particularly interesting 1,4-dicyano-substituted naphthalenes are those of formula

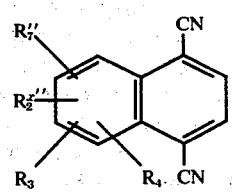
(31)

wherein $R_7''$ represents halogen, alkyl, alkylsulphonyl or arylsulphonyl, $R_2^{x''}$ represents hydrogen, halogen, alkyl or alkylsulphonyl, $R_3$ represents hydrogen, halogen or alkyl and $R_4$ represents hydrogen, halogen or alkyl, and also those of formula

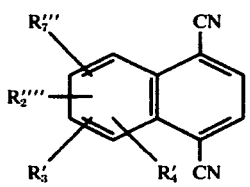 (32)

wherein $R_7'''$ represents halogen or alkyl, $R_2''''$ represents hydrogen, halogen or alkyl, $R_3'$ represents hydrogen or halogen, and $R_4'$ represents hydrogen or halogen.

Preeminent 1,4-dicyano-substituted naphthalenes are those of formula

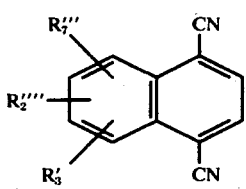 (33)

wherein $R_7'''$ represents halogen or alkyl, $R_2''''$ represents hydrogen, halogen or alkyl and $R_3'$ represents hydrogen or halogen, and also those of formula

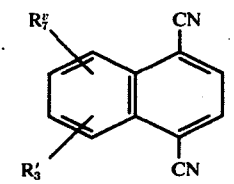 (34)

wherein $R_7^v$ represents halogen and $R_3'$ represents hydrogen or halogen.

Interesting naphthalene derivatives within the scope of the present invention are also those of formula

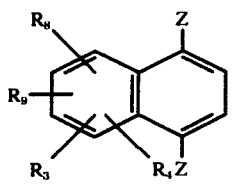 (35)

wherein Z represents carboxy, carbalkoxy or -CONY$_1$Y$_2$, wherein each of $Y_1$ and $Y_2$ independently represents hydrogen or alkyl, $R_8$ represents halogen, alkyl, alkoxy, carboxy, sulpho, $-SO_2NR_5R_6$, in which each of $R_5$ and $R_6$ independently represents hydrogen or alkyl, or together they complete a 5- or 6-membered heterocyclic ring, alkylsulphonyl, arylsulphonyl or nitro, $R_9$ represents hydrogen, halogen, alkyl, alkoxy, carboxy, alkylsulphonyl or nitro, $R_3$ represents hydrogen, halogen or alkyl, and $R_4$ represents hydrogen, halogen or alkyl.

Particularly interesting naphthalene derivatives are those of formula

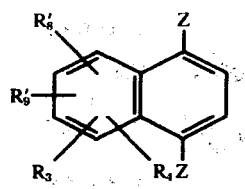 (36)

wherein Z is as defined hereinbefore, $R_8'$ represents halogen, alkyl, alkoxy, carboxy, alkylsulphonyl, arylsulphonyl or nitro, $R_9'$ represents hydrogen, halogen, alkyl, alkoxy, carboxy, alkylsulphonyl or nitro, $R_3$ represents hydrogen, halogen or alkyl, and $R_4$ represents hydrogen, halogen or alkyl, and also those of formula

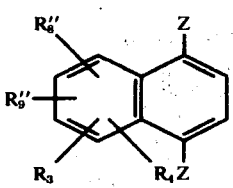 (37)

wherein Z is as defined hereinbefore, $R_8''$ represents halogen, alkyl, alkylsulphonyl or arylsulphonyl, $R_9''$ represents hydrogen, halogen, alkyl or alkylsulphonyl, $R_3$ represents hydrogen, halogen or alkyl, and $R_4$ represents hydrogen, halogen or alkyl.

Important naphthalene derivatives are those of formula

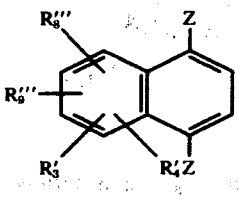 (38)

wherein Z is as defined hereinbefore, $R_8'''$ represents halogen or alkyl, $R_9'''$ represents hydrogen, halogen or alkyl, $R_3'$ represents hydrogen or halogen, and $R_4'$ represents hydrogen or halogen, and, in particular, those of formula

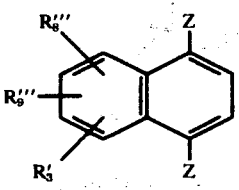 (39)

wherein Z is as defined hereinbefore, $R_8'''$ represents halogen or alkyl, $R_9'''$ represents hydrogen, halogen or alkyl, and $R_3'$ represents hydrogen or halogen, and also those of formula

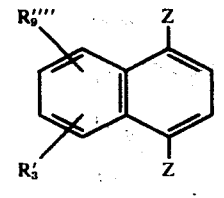 (40)

wherein Z is as defined hereinbefore, $R_9''''$ represents halogen, and $R_3'$ represents hydrogen or halogen.

The following Examples illustrate the invention, the parts being by weight unless otherwise stated.

EXAMPLE 1

15.6 parts of o-xylylene dicyanide and 8.5 parts of glyoxal hydrate (trimer) ($3C_2H_2O_2.2H_2O$), containing 80% of glyoxal to be liberated, are stirred in 200 parts of methanol. The reaction mixture is treated at 15° C, with stirring and under nitrogen, with 11.2 parts of powdered potassium hydroxide added by small amounts.

After addition of the potassium hydroxide, the reaction mixture is further stirred for 15 hours at room temperature and under nitrogen. The slightly brown coloured reaction mixture is then freed from methanol under vacuum and diluted with 500 parts by volume of water. The precipitated crude 1,4-dicyanonaphthalene is filtered off with suction and washed neutral with water. Yield: 11 parts of 1,4-dicyanonaphthalene (61.8% of theory) in the form of slightly brown coloured needles; m.p. 175°–185° C.

One recrystallisation from alcohol using 5 parts of activated carbon yields 5.5 parts of the compound

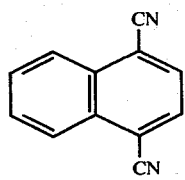

(101)

as fine needles with a melting point of 204°–205° C.

EXAMPLE 2

78 parts of o-xylylene dicyanide and 42 parts of glyoxal hydrate (trimer) ($3C_2H_2O_2.2H_2O$), containing 80% of glyoxal to be liberated, are stirred in 400 parts by volume of methanol. The reaction mixture is treated at 0° to 5° C, with stirring and under nitrogen, with 56 parts of powdered potassium hydroxide added by small amounts.

After the addition of potassium hydroxide, stirring is continued for 12 hours at 0° to 5° C under nitrogen. The slightly brown coloured reaction mixture is subsequently neutralised with dilute hydrochloric acid, freed from methanol under vacuum, and filtered with suction. The filter cake is washed neutral with water and dried in vacuo. Yield: 88 parts (99% of theory) of 1,4-dicyanonaphthalene of formula

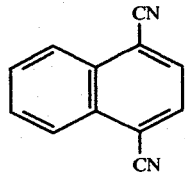

(102)

in the form of a slightly brown coloured powder with a melting point of 158° to 168° C.

The crude product is taken up in 700 parts by volume of 1,2-dichloroethane, treated with 50 parts by weight of sodium chloride and refluxed. Then 44.5 parts of phosphoroxy chloride in 50 parts by volume of 1,2-dichloroethane are slowly added dropwise. The reaction mixture is then refluxed for 5 hours, freed from insoluble constituents by filtration and concentrated to dryness in vacuo. Yield: 67 parts of 1,4-dicyanonaphthalene (75% of theory) in the form of a slightly brown coloured crystalline powder with a melting point of 198°–204° C.

EXAMPLE 3

21 parts of 4-tert. butyl-1,2-bis-cyanomethyl-benzene and 8.5 parts of glyoxal hydrate (trimer) ($3C_2H_2O_2.2H_2O$), containing 80% of glyoxal to be liberated, are stirred in 80 parts by volume of methanol. The reaction mixture is further stirred under nitrogen at 0° to 5° C and treated with 11.2 parts by weight of powdered potassium hydroxide added by small amounts.

After the addition of potassium hydroxide, stirring is continued for 5 hours at 0° to 5° under nitrogen. The slightly brown coloured reaction mixture is subsequently neutralised with dilute hydrochloric acid, freed from methanol in vacuo and extracted with methylene chloride. The methylene chloride extract is washed neutral with water, dried over sodium sulphate and concentrated to dryness in vacuo. Yield: 24 parts of a yellow oil which is chromatographed over aluminium oxide. Elution with chlorobenzene yields 4 parts (17% of theory) of 6-tert. butyl-1,4-dicyanonaphthalene of formula

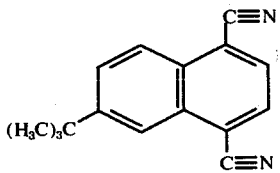

(103)

in the form of white crystals with a melting point of 138°–143° C. Two recrystallisations from alcohol yield small white needles which have a melting point of 148°–149° C. The 4-tert. butyl-1,2-bis-cyanomethyl-benzene used as starting material can be obtained, for example, as follows: 389 parts of 4-tert. butyl-o-xylene (manufactured in accordance with the particulars of B. W. Larner and A. T. Peters, J. Chem. Soc. 1952, 682) are diluted with 2000 parts by volume of carbon tetrachloride and treated with 855 parts of N-bromosuccinimide and 5 parts of dibenzoyl peroxide. The reaction mixture is slowly heated to reflux until the onset of the exothermic reaction. After the exothermic reaction has subsided, the reaction mixture is kept for 2 hours at reflux and then cooled to room temperature. The precipitated succinimide is collected by suction filtration and washed with carbon tetrachloride. Yield: 715 parts of a light brown oil which a gas chromatogram shows to have a content of 63.7% of 4-tert. butyl-$\alpha,\alpha'$-dibromo-o-xylene of formula

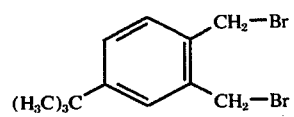

(104)

The product is distilled under a high vacuum. The fraction with a boiling range of 125°–130° C (0.05 Torr)

contains 450 parts of 4-tert. butyl-α,α'-dibromo-o-xylene, with a melting point of 54°-56° C, which is obtained as small white needles with a melting point of 58°-59° C after one recrystallisation from methanol.

286 parts of potassium cyanide are dissolved in 1200 parts by volume of water and 14 parts of benzyl-tri-n-butyl-ammonium bromide are added as phase transfer catalyst. To the strongly stirred reaction mixture, which is heated to 95° C, are added dropwise over the course of 15 minutes, after the heating has been removed, 640 parts by weight of molten 4-tert. butyl-α-α'-dibromo-o-xylene.

After the addition of the dibromo compound, the reaction mixture is stirred for a further 30 minutes at reflux, rapidly cooled with ice to room temperature, taken up in methylene chloride, and washed neutral with water. The methylene chloride layer is dried over sodium sulphate and freed from methylene chloride in vacuo. Yield: 402 parts of a yellowish brown oil which a gas chromatogram shows to have a 70.4% content of 4-tert. butyl-1,2-bis-cyanomethylbenzene of formula

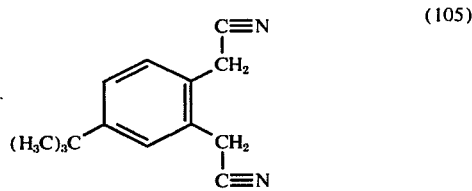
(105)

The product is distilled under a high vacuum. The fraction with a boiling range of 166°-170° C (0.08 Torr) contains 230 parts by weight of 4-tert. butyl-1,2-bis-cyanomethylbenzene with a melting point of 46°-48° C, which after one recrystallisation from methanol is obtained in the form of small, light yellow needles with a melting point of 48° C.

EXAMPLE 4

17 parts of 4,5-dimethyl-1,2-bis-cyanomethyl-benzene and 7.8 parts of glyoxal hydrate (trimer) (3C₂H₂O₂.2H₂O) containing 80% of glyoxal to be liberated, are stirred in 100 parts by volume of methanol. The reaction mixture is treated at 0° to 5° C, with stirring and under nitrogen, with 10.5 parts of powdered potassium hydroxide added by small amounts. After the addition of potassium hydroxide, stirring is continued for a further 5 hours at 0° to 5° C under nitrogen. The slightly brown coloured reaction mixture is subsequently neutralised with dilute hydrochloric acid, freed from methanol in vacuo and extracted with methylene chloride. The methylene chloride extract is washed neutral with water, dried over sodium sulphate and concentrated to dryness in vacuo. Yield: 18 parts of a brown oil which is chromatographed over aluminium oxide. Elution with chlorobenzene yields 6.5 parts (34% of theory) of 6,7-dimethyl-1,4-di-cyanonaphthalene of formula

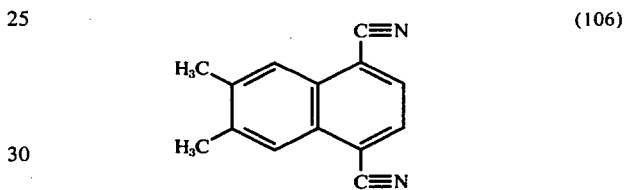
(106)

in the form of white crystals with a melting point of 212°-220° C. Two recrystallisations from alcohol yield small white needles with a melting point of 225°-227° C. The 4,5-dimethyl-1,2-cyanomethyl-benzene used as starting material can be obtained for example as follows according to the reaction scheme:

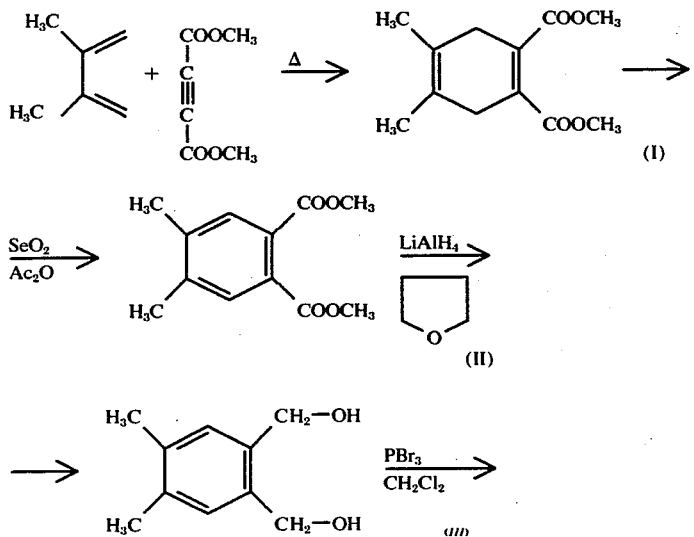

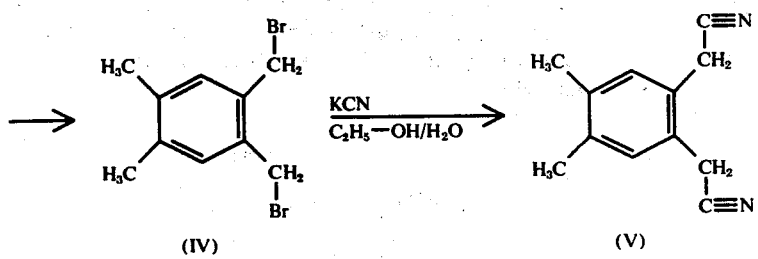

A. 5,6-dimethyl-1,4-dihydro-phthalic acid dimethyl ester (I)

A trace of hydroquinone is added first to 142 parts of acetylenedicarboxylic acid dimethyl ester and then 90 parts of 2,3-dimethyl-1,3-butadiene are slowly added dropwise. The temperature of the exothermic reaction may not exceed 70° C. The reaction mixture is subsequently kept for 2 hours at reflux (70° C) and then cooled to room temperature. A slightly yellow coloured oil is obtained which a gas chromatogram shows to have a 90.9% content of 5,6-dimethyl-1,4-dihydrophthalic acid dimethyl ester (I). The product is further reacted without purification.

B. 4,5-dimethyl-phthalic acid dimethyl ester (II)

232 parts of the 5,6-dimethyl-1,4-dihydro-phthalic acid dimethyl ester (I) obtained in A) are first freed from readily volatile constituents in vacuo and then diluted with 400 parts by volume of acetic anhydride. Then 133 parts of selenium dioxide are slowly added by small amounts to the reaction mixture, which is heated to 100° C, and the temperature rises to 130° C without external application of heat. The reaction mixture is subsequently refluxed for 3 hours and freed from acetic anhydride in vacuo. The residue is taken up in methylene chloride, the solution is freed from precipitated selenium by filtration, then freed from acid constituents with a saturated aqueous sodium bicarbonate solution, washed neutral with water, dried over sodium sulphate and concentrated to dryness in vacuo. Yield: 230 parts of a yellowish brown oil which a gas chromatogram shows to have a 94% content of 4,5-dimethyl-phthalic acid dimethyl ester (II). The product is distilled under a high vacuum. The fraction with a boiling range of 116°–120° C (0.04 Torr) contains 174 parts (78% of theory) of 4,5-dimethyl-phthalic acid dimethyl ester (II) with a melting point of 54°–55° C.

C. 4,5-Dimethyl-phthalic alcohol 58.5 parts of lithium aluminium hydride are suspended at room temperature, in an atmosphere of nitrogen, in 1500 parts by volume of anhydrous tetrahydrofuran. To the stirred suspension is added dropwise in the course of 2 hours a solution of 173 parts of 4,5-dimethyl-phthalic acid dimethyl ester (II) in 1000 parts by volume of anhydrous tetrahydrofuran. The reaction mixture is refluxed for 3 hours and then cooled to 10° C. Then 59 parts by volume of water, 59 parts by volume of 15% sodium hydroxide solution and 177 parts by volume of water are added in succession to the stirred, ice-cold reaction mixture. Stirring is continued for 1 hour, then the salts are filtered off and washed with tetrahydrofuran. The filtrate is dried over sodium sulphate and concentrated in vacuo to dryness. Yield: 102 parts (83% of theory) of 4,5-dimethyl-phthalic alcohol (II) in the form of a white crystalline powder with a melting point of 100°–103° C. After sublimation under a high vacuum, it is obtained in the form of white crystals with a melting point of 103°–104° C.

D. 4,5-Dimethyl-α,α'-dibromo-o-xylene (IV)

A solution of 165 parts of phosphorus tribromide in 500 parts by volume of methylene chloride is added dropwise in the course of 2 hours at room temperature to a solution of 100 parts of 4,5-dimethyl-phthalic alcohol in 1000 parts by volume of methylene chloride, in the process of which the temperature may not exceed 35° C. The reaction mixture is stirred for a further 3 hours at room temperature, then cooled to 10° C and diluted with 500 parts of water in the course of 10 minutes. The temperature remains below 25° C. The methylene chloride layer is separated, freed from acid constituents with 2 normal sodium carbonate solution, dried over sodium sulphate and concentrated to dryness in vacuo. Yield: 168 parts (95% of theory) of 4,5-dimethyl-α-α'-dibromo-o-xylene (IV) in the form of a white crystalline powder with a melting point of 116°–120° C which is obtained after one recrystallisation from alcohol in the form of small white needles with a melting point of 119°–120° C.

E. 4,5-Dimethyl-1,2-bis-cyanomethyl-benzene (V)

47 parts of potassium cyanide are dissolved in 100 parts by volume of water. The solution is diluted with 300 parts by volume of ethanol and refluxed. The 95 parts of powdered 4,5-α,α'-dibromo-o-xylene are added by small amounts in the course of 15 minutes while the reaction mixture remains under reflux without the application of heat. The reaction mixture is subsequently refluxed for 1 hour, rapidly cooled with ice, acidified with 2 normal hydrochloric acid and freed from ethanol in vacuo. The aqueous suspension is filtered with suction and the filter cake is washed neutral with water. Yield: 55 parts (91% of theory) of 4,5-dimethyl-1,2-bis-cyanomethyl-benzene (V) in the form of a yellow crystalline powder with a melting point of 95°–102° C. After one recrystallisation from alcohol with activated carbon it is obtained in the form of small, fine, pale yellow needles, which, after sublimation in a high vacuum, have a melting point of 103°–104° C.

EXAMPLE 5

12 parts of 3,4,5,6-tetrachloro-1,2-bis-cyanomethyl-benzene and 12 parts by volume of a 30% aqueous glyoxal solution are stirred in 240 parts of methanol. With stirring and under nitrogen, 4.8 parts of powdered potassium hydroxide are added to the reaction mixture by small amounts at −10° C and the temperature rises to −1° C.

After the addition of potassium hydroxide, stirring is continued for a further 5 hours at −10° C under nitrogen. The slightly brown coloured reaction mixture is subsequently neutralised with 2 normal hydrochloric acid, freed from methanol in vacuo and filtered with suction. The filter cake is washed neutral with water. Yield: 9 parts (70% of theory) of 5,6,7,8-tetrachloro-1,4-dicyanonaphthalene of formula

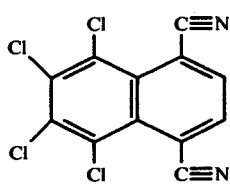
(107)

in the form of a light brown crystalline powder with a melting point of 215°–220° C. Small white needles which melt at 221°–222° C are obtained after two recrystallisations from alcohol with activated carbon.

The 3,4,5,6-tetrachloro-1,2-bis-cyanomethyl-benzene used as starting material can be obtained, for example, as follows:

160 parts of 3,4,5,6-tetrachloro-α,α'-dibromo-o-xylene are dissolved hot in 300 parts by volume of benzene. The solution is diluted with 600 parts by volume of methanol and refluxed. Then 41.2 parts of sodium cyanide are added by small amounts in the course of 15 minutes to the strongly stirred reaction mixture, which is further stirred for 1 hour under reflux, rapidly cooled to 0° C with ice and acidified with 400 parts by volume of 2 normal hydrochloric acid. The resultant yellow suspension is freed from methanol and benzene in vacuo, filtered with suction, and the filter cake is washed neutral with water. Yield: 110 parts (94% of theory) of 3,4,5,6-tetrachloro-1,2-bis-cyanomethyl-benzene of formula

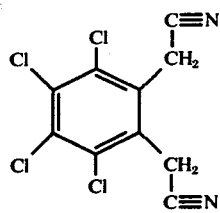
(108)

in the form of a yellow crystalline powder which melts at 182°–196° C. Two recrystallisations from chlorobenzene with 25 parts of activated carbon yields 32 parts of yellow needles with a melting point of 227°–229° C.

The 3,4,5,6-tetrachloro-α,α'-dibromo-o-xylene used as starting material was obtained in accordance with the particulars of German Auslegeschrift 1.568.607 and U.S. Pat. No. 2,702,825.

EXAMPLE 6

20 parts of 2,3-bis-cyanomethyl-naphthalene and 8.5 parts of glyoxal hydrate (trimer) ($3C_2H_2O_2.2H_2O$), containing 80% of glyoxal to be liberated, are stirred in a mixture of 300 parts by volume of methanol and 50 parts by volume of dimethyl sulphoxide. With stirring and under nitrogen, 11.2 parts of powdered potassium hydroxide are added by small amounts to the reaction mixture at 0° C to 5° C. After the addition of the potassium hydroxide, stirring is continued for 24 hours at room temperature under nitrogen. The slightly brown coloured reaction mixture is subsequently acidified with 200 parts by volume of 2 normal hydrochloric acid, freed from methanol in vacuo, diluted with 100 parts by volume of water and filtered with suction. The filter cake is washed neutral with water. Yield: 22.7 parts (100% of theory) of 1,4-dicyano-anthracene of formula

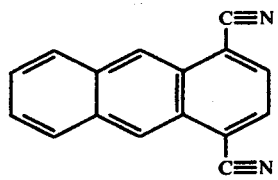
(109)

in the form of a brown crystalline powder with a melting point of 190°–225° C.

The crude product is taken up in methylene chloride and the solution is freed from insoluble constituents by filtration, decolourised with activated carbon an recrystallised from chlorobenzene. Two recrystallisations from chlorobenzene yield yellow needles with a melting point of 264°–265° C. The 2,3-bis-cyanomethyl-naphthalene was obtained from 2,3-dimethyl-naphthalene according to the particulars of W. Ried and H. Bodem, Ber. 89 708-12 (1956).

EXAMPLE 7

31.2 parts of o-xylylene dicyanide and 17 parts of glyoxal hydrate (trimer) ($3C_2H_2O_2.2H_2O$), containing 80% of glyoxal to be liberated, are stirred in 200 parts by volume of methanol. With stirring and under nitrogen, 21.6 parts of powdered sodium methylate are added to the reaction mixture by small amounts at 0° C to 5° C.

After addition of sodium methylate, stirring is continued for 5 hours at 0° to 5° C under nitrogen. The slightly brown coloured reaction mixture is subsequently diluted with 200 parts of ethanol, treated with 56 parts of powdered potassium hydroxide and slowly heated to 190° C under nitrogen, in the process of which the methanol is distilled off and ammonia escapes at 80° C. After it has been stirred for 15 hours at 185°–190° C under nitrogen, the reaction mixture is cooled to 100° C and diluted with 1000 parts by volume of water. The dark brown, clear solution is decolourised in a steam bath with 15 parts of activated carbon and acidified with 150 parts by volume of concentrated hydrochloric acid. The precipitated acid is filtered off hot with suction and the filter cake is washed neutral with water. Yield: 30 parts of naphthalene-1,4-dicarboxylic acid (69% of theory) in the form of a pale yellow crystalline powder with a melting point of 310°–315° C.

EXAMPLE 8

The reaction is carried out under the same conditions as described in Example 7, except that 22.4 parts of powdered potassium hydroxide are used instead of 21.6 parts of sodium methylate. Yield: 29 parts of naphthalene-1,4-dicarboxylic acid (67% of theory) in the form of a pale yellow crystalline powder with a melting point of 310°–315° C.

EXAMPLE 9

38 parts of 4-chloro-1,2-bis-cyanomethyl-benzene and 17 parts of glyoxal hydrate (trimer) ($3C_2H_2O_2.2H_2O$), containing 80% of glyoxal to be liberated, are stirred in 150 parts by volume of methanol. With stirring and under nitrogen, 16 parts of powdered sodium hydroxide are added to the reaction mixture by small amounts at 0° to 5° C.

After the addition of sodium hydroxide, stirring is continued for 5 hours at 0° to 5° C under nitrogen. The slightly brown coloured reaction mixture is subsequently treated with 200 parts by volume of 80% sulphuric acid and 80 parts by volume of glacial acetic acid and slowly heated to 140° C under nitrogen while distilling off the methanol. After it has been stirred for 5 hours at 140°–150° C under nitrogen, the reaction mixture is cooled to 150° C and diluted with 500 parts of water. The precipitate is filtered off with suction, washed neutral with water and taken up in 500 parts by volume of water. Then 60 parts by volume of 30% sodium hydroxide solution are added and the dark brown solution is decolourised in a steam bath with 15 parts of activated carbon and acidified with 150 parts by volume of concentrated hydrochloric acid. The precipitated acid is filtered off hot and the filter cake is washed neutral with water. Yield: 34 parts of 6-chloro-naphthalene-1,4-dicarboxylic acid (68% of theory) of formula

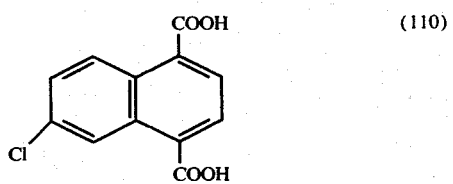

(110)

in the form of slightly brown crystalline powder with a melting point of 278°–280° C.

small, pale yellow needles are obtained after one recrystallisation from glacial acetic acid; melting point 281°–283° C.

The 4-chloro-1,2-bis-cyanomethyl-benzene used as starting material was obtained according to the particulars of A. S. Dey, A. Rosowsky and E. J. Modest, J. Org. Chem. 1970 536-9.

EXAMPLE 10

106 parts of 4-tert. butyl-1,2-bis-cyanomethyl-benzene and 42 parts of glyoxal hydrate (trimer) (3$C_2H_2O_2$·2$H_2O$), containing 80% of glyoxal to be liberated, are stirred in 400 parts by volume of methanol. With stirring and under nitrogen, 56 parts of potassium hydroxide are added to the reaction mixture by small amounts at 0° to 5° C.

After the addition of potassium hydroxide, stirring is continued for 5 hours at 0° to 5° C. The slightly brown coloured reaction mixture is subsequently diluted with 250 parts of ethylene glycol and then, after addition of 84 parts of powdered potassium hydroxide, slowly heated to 190° C under nitrogen while the methanol is distilled off and ammonia escapes at 80° C. After it has been stirred for 5 hours at 185° to 190° C under nitrogen, the reaction mixture is worked up as described in Example 7.

Yield: 89 parts of 6-tert. butyl-naphthalene-1,4-dicarboxylic acid (65% of theory) of formula

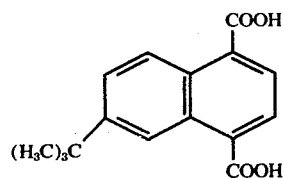

(111)

in the form of a light brown crystalline powder with a melting point of 276°–279° C.

Small, pale yellow needles with a melting point of 286°–288° C are obtained after one recrystallisation from glacial acetic acid with activated carbon. The 4-tert. butyl-1,2-bis-cyanomethyl-benzene can be obtained as described in Example 3.

EXAMPLE 11

18.4 parts of 4,5-dimethyl-1,2-bis-cyanomethyl-benzene and 8.4 parts of glyoxal hydrate (trimer) (3$C_2H_2O_2$·2$H_2O$), containing 80% of glyoxal to be liberated, are stirred in 100 parts by volume of methanol. With stirring and under nitrogen, 11.2 parts of powdered potassium hydroxide are added to the reaction mixture by small amounts at 0° to 5° C. After the addition of potassium hydroxide, stirring is continued for 5 hours at 0° to 5° C under nitrogen. The slightly brown coloured reaction mixture is subsequently diluted with 100 parts by volume of ethylene glycol and then, after addition of 28 parts of potassium hydroxide, heated slowly to 190° C under nitrogen while the methanol is distilled off and ammonia escapes at 80° C. After it has been stirred for 5 hours at 185° to 190° C under nitrogen, the reaction mixture is worked up as described in Example 7 to yield 7.5 parts of 6,7-dimethyl-naphthalene-1,4-dicarboxylic acid (31% of theory) of formula

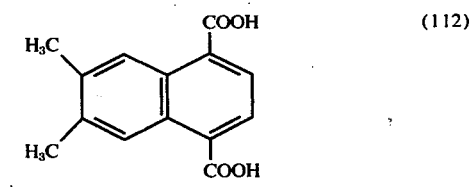

(112)

in the form of slightly brown crystalline powder with a melting point of 268°–280° C. Small, pale yellow needles with a melting point of 288°–291° C are obtained after one recrystallisation from glacial acetic acid with activated carbon. The 4,5-dimethyl-1,2-bis-cyanomethyl-benzene used as starting material can be obtained as described in Example 4.

EXAMPLE 12

12 parts of 3,4,5,6-tetrachloro-1,2-bis-cyanomethyl-benzene and 12 parts by volume of a 30% aqueous glyoxal solution are stirred in 240 parts of methanol. With stirring and under nitrogen, 4.8 parts of powdered potassium hydroxide are added to the reaction mixture by small amounts at −10° C and the temperature rises to =1° C.

After the addition of potassium hydroxide, stirring is continued for 5 hours at −10° C under nitrogen. The slightly brown coloured reaction mixture is subsequently treated with 80 parts by volume of 80% sulphuric acid and 15 parts by volume of glacial acetic and slowly heated to 140° C under nitrogen while distilling off the methanol. After it has been stirred for 5 hours at 140° to 150° C under nitrogen, the reaction mixture is cooled to 100° C and diluted with 200 parts by volume of water. The precipitate is filtered off with suction, washed neutral with water and dried under vacuum at 100° C.

Yield: 12 parts of 5,6,7,8-tetralchloro-naphthalene-1,4-dicarboxylic acid (85% of theory) of formula

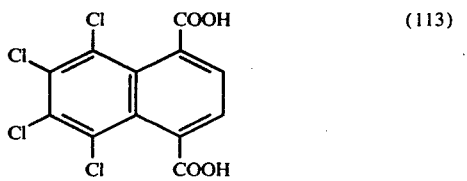

in the form of a brownish black crystalline powder with a melting point of 285°–290° C.

The crude product is taken up in 200 parts by volume of water and 30 parts by volume of aqueous 30% sodium hydroxide solution are added to the solution. The dark brown solution is decolourised in a steam bath with 5 parts of activated carbon and acidified with 100 parts by volume of concentrated hydrochloric acid. The precipitated acid is filtered off hot and the filter cake is washed neutral with water. Two recrystallisations from glacial acetic acid yields 2 parts of small white needles with a melting point of 319°–321° C.

The 3,4,5,6-tetrachloro-1,2-bis-cyanomethyl-benzene used as starting material can be obtained as described in Example 5.

EXAMPLE 13

40 parts by weight of 2,3-bis-cyanomethyl-naphthalene and 17 parts by weight of glyoxal hydrate (trimer) ($3C_2H_2O_2 \cdot 2H_2O$), containing 80% of glyoxal to be liberated, are stirred in a mixture of 600 parts by volume of methanol and 100 parts by volume of dimethyl sulphoxide. With stirring and under nitrogen, 22.4 parts of powdered potassium hydroxide are added to the reaction mixture by small amounts at 0° to 5° C. After the addition of potassium hydroxide, stirring is continued for 24 hours at room temperature under nitrogen. The slightly brown coloured reaction mixture is subsequently acidified with 200 parts by volume of 2 normal hydrochloric acid, freed from methanol in vacuo, diluted with 200 parts by volume of water, filtered with suction and the filter cake is washed neutral with water.

The moist filter cake is taken up in 300 parts by volume of ethylene glycol and the solution, after addition of 36 parts of powdered potassium hydroxide, is slowly heated to 180° C under nitrogen while the methanol is distilled off and ammonia escapes at 80° C. After it has been stirred for 5 hours at 170° to 180° C under nitrogen, the reaction mixture is worked up as described in Example 7. Yield: 29 parts of anthracene-1,4-dicarboxylic acid (55% of theory) of formula

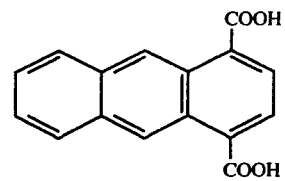

in the form of a yellowish red crystalline powder with a melting point of 301°–302° C.

Small, yellowish red needles with a melting point of 303°–304° C are obtained after one recrystallisation from glacial acetic acid with activated carbon.

The 2,3-bis-cyanomethyl-naphthalene used as starting material was obtained according to the particulars of W. Ried and H. Bodem, Ber. 89, 708-12 (1956).

15 parts of anthracene-1,4-dicarboxylic acid are stirred in 200 parts by volume of chlorobenzene and 0.5 part by volume of dimethyl formamide. The reaction mixture is refluxed and treated dropwise with 20 parts of thionyl chloride, whereupon a clear solution is obtained. After refluxing for 1 hour, excess thionyl chloride is distilled off with about 100 parts by volume of chlorobenzene and the reaction mixture is cooled to room temperature. Then 100 parts by volume of ethanol are added and the clear solution is refluxed for a further hour and concentrated to dryness is vacuo. One recrystallisation from ethanol with activated carbon yields 12 parts of anthracene-1,4-dicarboxylic acid diethyl ester (66% of theory) of formula

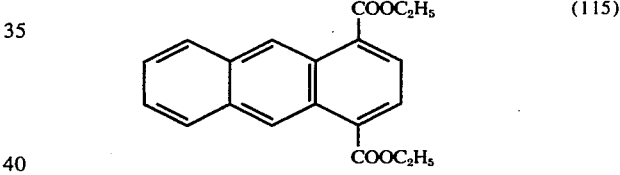

in the form of long yellow needles with a melting point of 99°–100° C.

What I claim is:

1. A process for the manufacture of bicyclic or tricyclic compounds of formula

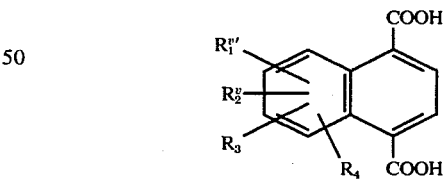

wherein $R_1^{v'}$ represents hydrogen, halogen, alkyl, alkoxy, carboxy, sulpho, —$SO_2NR_5R_6$, wherein each of $R_5$ and $R_6$ independently represents hydrogen or alkyl, or together they complete a 5- or 6-membered heterocyclic ring, alkylsulphonyl, arylsulphonyl, nitro, or together with $R_2^v$ completes a 6-membered aromatic ring or represents the methylenedioxy radical, $R_2^v$ represents hydrogen, halogen, alkyl, alkoxy, carboxy, alkylsulphonyl, nitro, or together with $R_1^{v'}$ completes a 6-membered aromatic ring or represents the methylenedioxy radical, $R_3$ represents hydrogen, halogen or alkyl, and $R_4$ represents hydrogen, halogen or alkyl, which process comprises reacting at a temperature below 50° C an o-xylylene dicyanide of formula

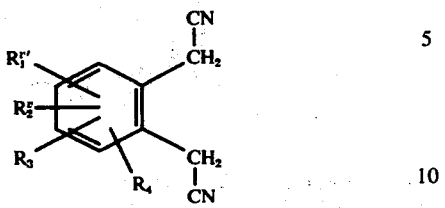

wherein $R_1^{v'}$, $R_2^v$, $R_3$ and $R_4$ are as defined hereinbefore, with glyoxal in the presence of a base and a solvent, and saponifying the resultant reaction product, without isolating it, with an acid or a base, at temperatures above 50° C.

2. A process according to claim 1 for the manufacture of bicyclic or tricyclic compounds of formula

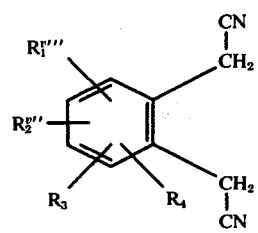

wherein $R_1^{v''}$ represents hydrogen, halogen, alkyl, carboxy, alkylsulphonyl, arylsulphonyl, nitro, or together with $R_2^{v'}$ completes a 6-membered aromatic ring or represents the methylenedioxy radical, $R_2^{v'}$ represents hydrogen, halogen, alkyl, alkoxy, alkylsulphonyl, or together with $R_1^{v''}$ completes a 6-membered aromatic ring or represents the methylenedioxy radical, $R_3$ represents hydrogen, halogen or alkyl, and $R_4$ represents hydrogen, halogen or alkyl, which process comprises reacting an o-xylylene dicyanide of formula

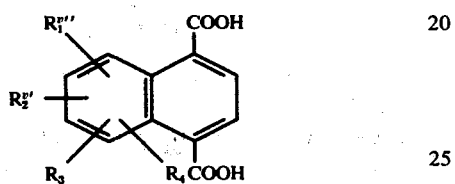

wherein $R_1^{v''}$, $R_2^{v'}$, $R_3$ and $R_4$ are as defined hereinbefore, with glyoxal.

3. A process according to claim 1 for the manufacture of bicyclic or tricyclic compounds of formula

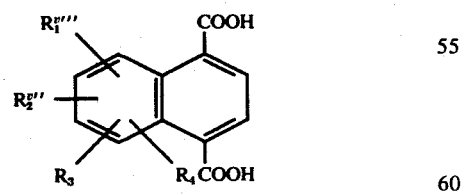

wherein $R_1^{v'''}$ represents hydrogen, halogen, alkyl, alkylsulphonyl, arylsulphonyl, or together with $R_2^{v'''}$ completes a 6-membered aromatic ring, $R_2^{v'''}$ represents hydrogen, halogen, alkyl, alkylsulphonyl, or together with $R_1^{v''''}$ completes a 6-membered aromatic ring, $R_3$ represents hydrogen, halogen or alkyl, and $R_4$ represents hydrogen, halogen or alkyl, which process comprises reacting an o-xylylene dicyanide of formula

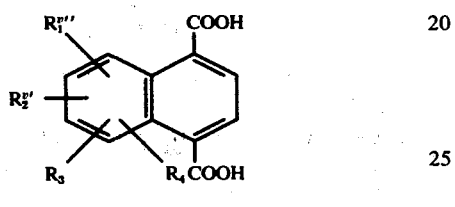

wherein $R_1^{v'''}$, $R_2^{v'''}$, $R_3$ and $R_4$ are as defined hereinbefore, with glyoxal.

4. A process according to claim 1 for the manufacture of bicyclic or tricyclic compounds of formula

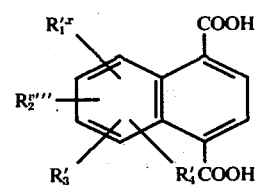

wherein $R_1'^x$ represents hydrogen, halogen or alkyl, or together with $R_2^{v'''}$ completes a 6-membered aromatic ring, $R_2^{v'''}$ represents hydrogen, halogen or alkyl, or together with $R_1'^x$ completes a 6-membered aromatic ring, $R_3'$ represents hydrogen or halogen, and $R_4'$ represents hydrogen or halogen, which process comprises reacting an o-xylylene dicyanide of formula

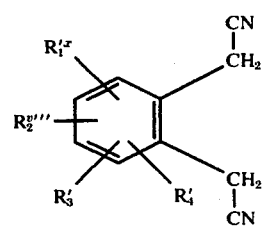

wherein $R_1'^x$, $R_2^{v'''}$, $R_3'$ and $R_4'$ are as defined hereinbefore, with glyoxal.

5. A process according to claim 1 for the manufacture of naphthalene-1,4-dicarboxylic acids of formula

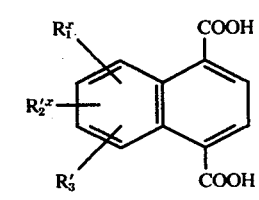

wherein $R_1^x$ represents hydrogen, halogen or alkyl, $R_2'^x$ represents hydrogen, halogen or alkyl, and $R_3'$ represents hydrogen or halogen, which comprises reacting an o-xylylene dicyanide of formula

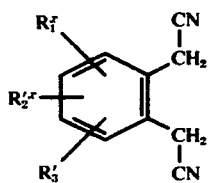

wherein $R_1^x$, $R_2'^x$ and $R_3'$ are as defined hereinbefore, with glyoxal.

6. A process according to claim 1 for the manufacture of naphthalene-1,4-dicarboxylic acids of formula

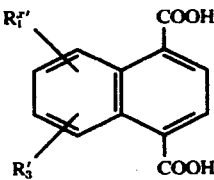

wherein $R_1^{x'}$ represents hydrogen or halogen and $R_3'$ represents hydrogen or halogen, which comprises reacting an o-xylylene dicyanide of formula

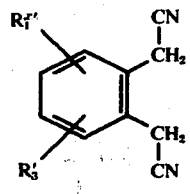

wherein $R_1^{x'}$ and $R_3'$ are as defined hereinbefore, with glyoxal.

7. A process according to claim 1 for the manufacture of the naphthalene-1,4-dicarboxylic acid of formula

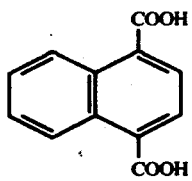

which comprises reacting an o-xylylene dicyanide of formula

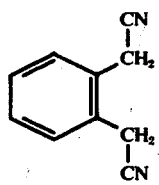

with glyoxal.

* * * * *

UNITED STATES PATENT OFFICE
CERTIFICATE OF CORRECTION

PATENT NO. : 4,011,261
DATED : March 8, 1977
INVENTOR(S) : LEONARDO GUGLIELMETTI It is certified that error appears in the above-identified patent and that said Letters Patent are hereby corrected as shown below:

In column 25, claim 3, line 62, change "$R_1^{V''}$" to -- $R_1^{V'''}$ --.

Signed and Sealed this

Third Day of May 1977

[SEAL]

Attest:

RUTH C. MASON
*Attesting Officer*

C. MARSHALL DANN
*Commissioner of Patents and Trademarks*